United States Patent [19]

Woodroof

[11] 4,303,712

[45] Dec. 1, 1981

[54] FABRIC SILICONE ELASTOMER COMPOSITE

[76] Inventor: E. Aubrey Woodroof, 16646 Mt. Cachuma Cir., Fountain Valley, Calif. 92708

[21] Appl. No.: 27,679

[22] Filed: Apr. 6, 1979

Related U.S. Application Data

[63] Continuation-in-part of Ser. No. 5,319, Jan. 22, 1979, abandoned.

[51] Int. Cl.³ ............................................. B32B 3/00
[52] U.S. Cl. ..................................... 428/58; 428/61; 428/220; 428/252; 428/253; 428/267; 428/286; 428/290; 428/447; 428/475.5
[58] Field of Search ............... 428/57, 58, 61, 102, 428/103, 230, 253, 254, 245, 267, 447, 220, 252, 286, 290, 475.5

[56] References Cited

U.S. PATENT DOCUMENTS

| | | | |
|---|---|---|---|
| 3,010,114 | 11/1961 | Lipschultz | 428/103 |
| 3,246,621 | 4/1966 | Copeland | 428/102 X |
| 3,264,155 | 8/1966 | Rhee | 428/230 X |
| 3,294,617 | 12/1966 | Way | 428/61 |
| 3,420,731 | 1/1969 | Kuhn | 428/58 |
| 3,455,306 | 7/1969 | Spanel | 428/230 X |
| 3,637,427 | 1/1972 | Tsuruta et al. | 428/254 X |
| 3,639,154 | 2/1972 | Sawa et al. | 428/254 |
| 3,668,001 | 6/1972 | Osaka et al. | 428/230 X |
| 3,814,658 | 6/1974 | Decker | 428/267 X |
| 3,817,818 | 6/1974 | Rowtenstall et al. | 428/253 X |
| 3,978,259 | 8/1976 | Hilton | 428/447 X |
| 4,128,675 | 12/1978 | Rössler et al. | 428/447 X |

*Primary Examiner*—Marion McCamish
*Attorney, Agent, or Firm*—Smyth, Pavitt, Siegemund & Martella

[57] ABSTRACT

A fabric elastomer composite includes a relatively thin elastomer membrane having a stretchable fabric joined thereto. The composite is thin, lightweight, waterproof but vapor permeable, and stretchable at least 100% in each direction. Various garments such as athletic wear and thermal products may be fabricated which are warm, waterproof and stretchable. Various types of joints are disclosed to assure watertight qualities.

14 Claims, 6 Drawing Figures

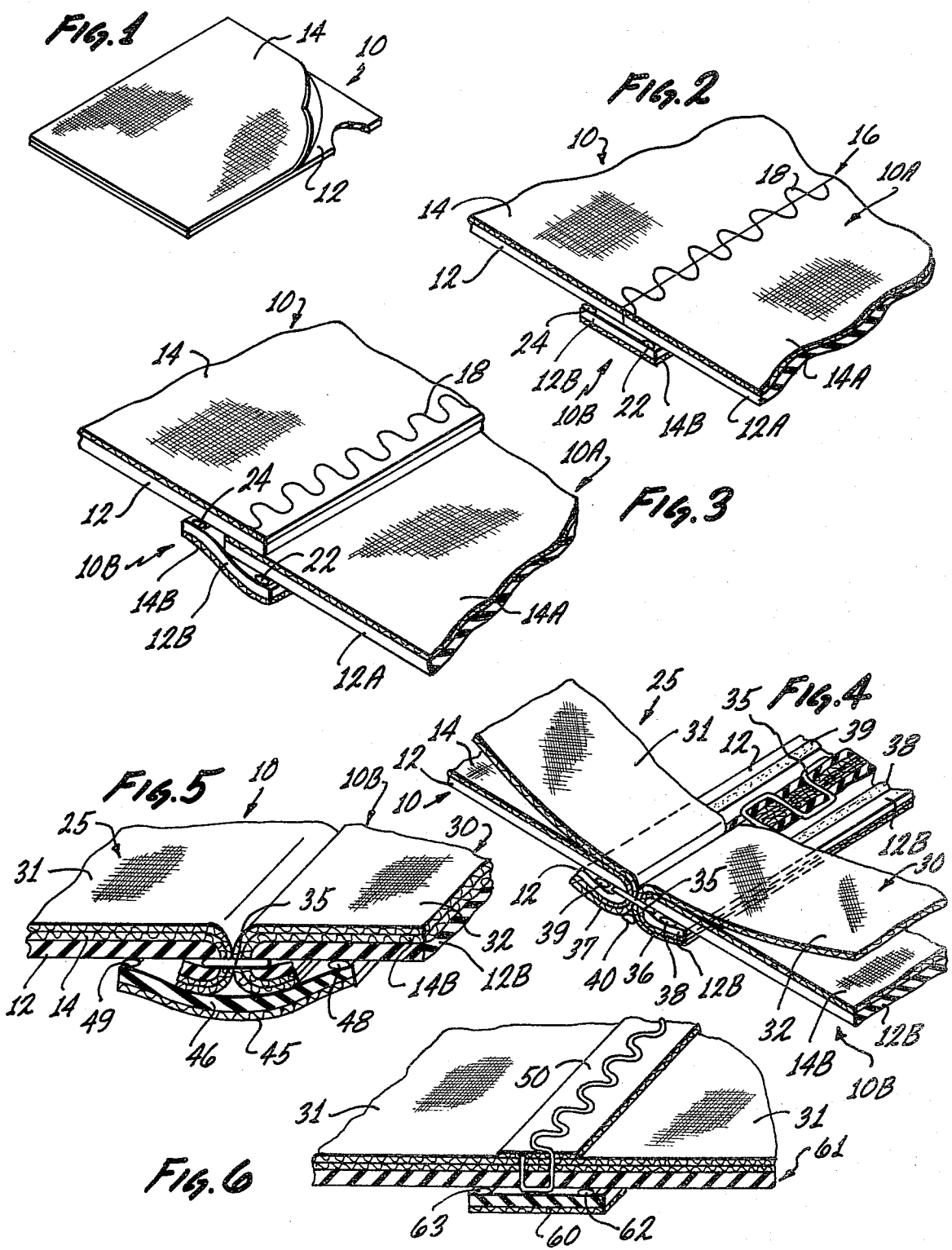

FABRIC SILICONE ELASTOMER COMPOSITE

This application is a continuation-in-part of U.S. application Ser. No. 5,319, filed Jan. 22, 1979 now abandoned.

BACKGROUND OF THE INVENTION

This invention relates to a fabric elastomer composite, the methods of making the same and to products incorporating the same and more particularly, to an improved fabric elastomer composite which is waterproof, "breathable", flexible and which can be used in the fabrication of improved products.

There are many instances in which a fabric elastomer composite in the form of a uniform, thin, semipermeable membrane is needed. One such type of product is that described in the above identified application. Other types of products include membranes for scientific measuring instruments such as ion specific electrodes, polarographic electrodes and other electro chemical devices, as well as membranes useable with both instrumentation and apparatus in the medical and scientific fields.

Additionally, fabric elastomer composites which are relatively inexpensive to manufacture, find utility in certain types of garments such as those used in skiing, foul weather garments, and garments to be used in extremely cold weather. Various types of garments used in various types of sports such as jogging and the like, are sometimes fabricated so as to induce perspiration for the purposes of weight reduction.

In other instances, the garment is designed principally to permit breathing. Unfortunately, those garments which permit breathing sometimes permit water to pass through the garment. In many instances those garments which do not permit water in liquid form to pass through the garments are subject to the objection that the wearer or user, if engaged in an activity which creates perspiration, may be as wet from the moisture which collects on the inside of the garment as if liquid passed through the garment.

There is available commercially a product known as Gore-Tex which is in the form of a laminated nylon product. It is described as a microporous product which sheds liquid water but allows water vapor to pass through the material.

In the case of ski clothing, it is not unusual to find products composed of nylon-laminated neoprene. Other products include stretch nylon material with needle punch polyester bonded of tricot for stretch insulation.

In general, the products above referred to incorporate the features of thermal insulation, stretchability, and lightweight.

Also known are laminates of velour fabrics such as nylon, dacron, (polyester) rayon, teflon, and polypropylene. Nylon velour materials incorporating polypeptide films and polycaprolactone have been critized because of the tendency of the films to crack.

There is considerable literature relating to the use of silicone rubber membranes, see Medical Instrumentation, Volume 7, number 4 268, 275 September-October 1973; fabric reinforced silicone membranes, Medical Instrumentation, Volume 9 number 3, 124–128, May-June 1975. U.S. Pat. No. 3,267,727 also described the formation of ultra thin polymer membranes.

SUMMARY OF THE INVENTION

The product in process of the present invention differs from the prior art by providing a composite fabric elastomer material from a thin film of thermo-plastic (for example silicone rubber), and a knitted or woven fabric (for example nylon).

The characteristics of the product of the present invention include warmth and the ability to be fabricated into warm, thermal garments. The product is lightweight, thin and flexible, as well as being windproof. The product is also vapor permeable but liquid impermeable and quite stretchable in each direction. Significantly, all of the above properties are retained after laundering, as by dry cleaning.

Accordingly, the product of the present invention includes a firmly knitted fabric having at least 100% elongation in each direction partially embedded and secured to a thin layer of thermo-plastic material, e.g. silicone rubber. The silicone rubber has a thickness in the range of 0.0006 to 0.0020 inches, plus or minus 0.0003 inches and is sufficiently thin to act as a membrane with controlled passage of water vapor there through e.g. 10 to 50 grams per meter squared, measured at 37° C. for 24 hours. Such vapor passage is in the range comparable to the moisture vapor transmission rate of human skin.

The fabric elastomer composite of the present invention is also non-toxic and free of extractable biologicals capable of causing irratation when in contact with human skin. The latter quality is of practical importance where the product of this invention is used in garments worn by those engaged in physical exercise, e.g.-ski wear, jogging suits and the like.

Since the membrane is liquid impermeable, it offers the advantage of being waterproof but vapor permeable thus permitting passage of water vapor but not water in liquid form.

When used with other materials in the fabrication of apparel type products, such products can be found with watertight seams while maintaining the desired qualities of being relatively stretchable, warm, waterproof but vapor permeable and windproof.

The fabric elastomer composite of this invention is easily fabricated, with accurate control of the membrane thickness, one important factor in providing the "breathability" of the present product.

It will be apparent from the foregoing and the following detailed description and specific examples that a much improved fabric elastomer composite having unique properties has been provided and can be used to fabricate unique apparel type products or used as membrane material in scientific and medical instrumentation. The further advantages, and features of the present invention may be understood with reference to the following detailed description of the invention.

DETAILED DESCRIPTION OF THE DRAWINGS

FIG. 1 is a view partly in section and partly in elevation of the fabric elastomer product in accordance with the present invention;

FIG. 2 is a view partly in section and partly in elevation of the fabric elastomer product of this view illustrating one form of a watertight joint in accordance with this invention;

FIG. 3 is a view partly in section and partly in elevation of the fabric elastomer product of this invention illustrating another form of watertight joint in accordance with this invention;

FIG. 4 is a view partly in section and partly in elevation of a garment type product in accordance with this invention illustrating the structure thereof and the formation of a watertight seam in accordance with this invention;

FIG. 5 is a view similar to that of FIG. 4 illustrating another form of watertight joint or seam; and FIG. 6 is a view similar to FIG. 4 showing a form of a seam to be used to provide a watertight seam in sewn areas of the garment.

DETAILED DESCRIPTION OF THE INVENTION

Referring to the drawings which illustrate preferred forms of the present invention, FIG. 1 illustrates the fabric elastomer composite 10 in accordance with the present invention. As shown the composite 10 includes a membrane thin elastomer 12 having a fabric material 14 joined thereto, as will be described.

In a preferred form, the composite possesses good tensile strength, has an elongation of at least 100% in each direction, non-toxic, non-pyrogenetic, non-antigenetic, and stable at relatively high and low temperatures. In addition to the above properties, the composite is vapor permeable while being liquid impermeable, i.e. waterproof, and windproof. This is achieved by controlling the thickness of the elastomer membrane in the range of 0.0006 to 0.0020 inches, plus or minus 0.0003 inches, a thickness which is sufficiently thin to provide a membrane action. The water vapor transmission through human skin, i.e. 10 to 50 grams per meter squared, measured at 37° C. for 24 hours. In effect, the elastomer membrane acts as human skin as far as vapor transmission and liquid impermeability is concerned. In a preferred form, the membrane is a silicone rubber such as dimethyl silicone elastomer, a material which is heat curable. A typical such material is supplied as a 13% dispersion of the silicone rubber in an organic solvent (chlorinated hydrocarbon) and is available under the trade designation Dow Corning Q 7-2213. It will be apparent to those skilled in the art that other materials may be used.

The fabric component 14, in accordance with this invention acts as a reinforcent and is preferably a timely knitted fabric material such as dacron, and preferably nylon, of 25 denier or less and which has at least 100% elongation in all directions. A typical such material is an 18/3 nylon fabric mesh having 150% by 240% elongation and available from Hanes Corporation. Another material which may be used, but which is not universally stretchable in all directions is an 18/3 nylon mesh having 300% by 50% elongation, again available from Hanes Corporation.

The fabric elastomer composite 10 of FIG. 1 may be fabricated a number of ways, but the preferred method in accordance with the present invention involves close control of the thickness of the wet elastomer layer thereby controlling the thickness of the cured material within the limits defined so that the proper moisture vapor transport quality is achieved. Accordingly, a relatively thin plastic sheet (0.002 inches) of Mylar (polyethylene terephthalate) of appropriate length and width is placed on a flat smooth surface and immobilized to eliminate wrinkles. The exposed upper surface of the plastic is cleaned with a lint free towel saturated in a volatile alcohol such as isopropyl alcohol.

After surface preparation, a thin layer of the silicone dispersion is applied over the plastic by a precision layering tool. One such tool is a precision layering doctor blade although other devices may be used, e.g. roller and the like, as is well known in the art.

The thickness of the cured elastomer is roughly 10% of the wet film thickness, the wet material being sufficient viscous so that flow does not occur. Thus various thicknesses of material may be found, as per the following table:

| Wet film thickness in inches | Cured membrane thickness in inches |
|---|---|
| 0.006 | 0.0006 |
| 0.008 | 0.0008 |
| 0.010 | 0.0010 |
| 0.012 | 0.0012 |
| 0.014 | 0.0014 |
| 0.016 | 0.0016 |
| 0.018 | 0.0018 |
| 0.020 | 0.0020 |

The wet layer is allowed to remain at room temperature for at least 15 minutes to allow the volatile solvent to evaporate and then oven cured for at least 15 minutes at 150° C. During heat curing, the assembly is maintained in a horizontal flat plane to assure proper uniform thickness. After curing, the assembly is removed from the oven and allowed to cool to room temperature.

Thereafter, a second layer of wet elastomer dispersion is applied over the cured first layer while the latter is still supported on the thin plastic support sheet. The width of the second layer is greater than the cured silicone first layer, the wet thickness again being in the range indicated previously. Immediately after the second wet layer is applied, the elastic nylon fabric of a dimension equal to the dimension of the cured layer is applied in an unstretched condition, over the wet layer. The thickness of the nylon fabric is about 0.0090 inches. The wet elastomer wets and partially surrounds the strands of the nylon mesh such that the latter is in unstretched or "relaxed" state, is embedded partially in the wet film but does not penetrate through the cured film.

The composite assembly is allowed to sit at room temperature for about 15 minutes for solvent evaporation and then placed in an oven in a flat horizontal plane and again cured at 150° C. for at least 15 minutes. After curing the cured composite is removed and allowed to cool to room temperature for about 10 minutes. The cured fabric elastomer composite is removed from the plastic support sheet by immersing the entire assembly in a 2:1 mixture of toluene in isopropyl alcohol and gently lifting the swollen fabric elastomer composite off the plastic support sheet. The separate swollen composite is placed on an absorbent material e.g. paper towels, and allowed to sit at room temperature until the solvent evaporates. The composite 10 is then trimmed to the length and width dimensions of the first cured elastomer to provide the product shown in FIG. 1.

In the event that examination of the composite 10 indicates any pin-holes or tears, these are easily repaired by the use of a patch whose structure is the same as the composite. In patching, a room temperature vulcanizing silicone (RTVS) is used, e.g. an almost 99% solid silicone rubber dispersion in 1% solvent such as acetic acid. A head of RTVS is placed around the defect on the silicone surface (12) of the composite 10. The patch, somewhat larger than the defect is placed over the head with the silicone face of the patch facing the silicone face of the composite, i.e. elastomer-to-elastomer facing relation, and pressed flat over the defect. As the RTVS cures at room temperature, the two facing surfaces of the elastomer bond to each other. Patching can also be conducted by bonding the elastomer side of the patch to the fabric side of the composite using RTVS or vice versa. Where elastomer fabric facing patching is used, care must be taken to assure that there is an elastomer-to-elastomer bond so as to preserve the desired membrane qualities of the composite.

The resultant fabric elastomer composite 10, especially those that are patch free may be used as a biocompatible and blood compatible material as described in application Ser. No. 5,319, supra, or as a membrane for electrodes or the like in scientific and medical devices.

Whether patch free or not, the composite possesses unique properties which render it highly desirable for use in various types of specialty garments, as noted. For example, using the "patch" technique described, various garments can be fabricated which have highly desirable properties.

More specifically, incorporation of the fabric elastomer composite 10 of this invention into garments permits the fabrication of warm multi-layer garments by virtue of the windproof nature of the composite. The garments are lightweight, waterproof, flexible and vapor permeable. Good tensile strength is provided in addition to stretchability. The composite is permeable to $CO_2$, $O_2$, and other gases and moisture vapor but impermeable to fluids, cations and anions. The material is stable at high temperature, e.g. 150° C., permeable organic liquids and stable in cleaning fluids such as dry cleaning solvents and the like.

Referring now to FIG. 2, wherein the same reference numerals have been used for the same components, two separate pieces of composite 10 and 10A, each including elastomer 12 and 12A and fabric 14 and 14A are joined together in a butt joint 16 using a serpentine stitch 18. Waterproofing is accomplished by use of a fabric elastomer strip 10B having elastomer 12B and fabric 14B components as described.

A head of RTVS is placed on each side 22 and 24 and along the periphery of the stitch 18 such that the stitching is between the beads, applied to the elastomer faces 12 and 12A of the composites 10 and 10A. The strip 10B is wide enough to extend beyond the beads and long enough to extend the width of the joint, the elastomer face 12B facing the elastomer faces 12 and 12A. Optionally, the ends of the strip may be sealed by transverse RTVS beads, not shown.

The joint illustrated in FIG. 2 may be used to form long pieces for garment production or to seal end pieces in garment fabrication.

The lap joint in FIG. 3 is similar to that of FIG. 2 and offers additional strength by lapping the joined pieces 10 and 10A, by a serpentine stitch 18 over and through the lapped area.

FIG. 4 illustrates a joint between two pairs 25 and 30 of composite 10 and 10B and fabric 31 and 32 components. Composites 10 and 10B are as described. Fabrics 31 and 32 may be fabric such as stretchable nylon or fabrics for thermal insulation and the like. The fabrics 31 and 32 are shown facing the fabric component 14 and 14B of the composites, the assembly being held together by stitching 35 such that the fabrics 31 and 32 contact each other which the free ends 36 and 37 of the composite are arranged so that the elastomer 12 and 12B are in facing relation, as shown. The length of the stitching one each side thereof includes an RTVS bead 38, 39 to waterproof the stitch 35 on each side while a third RTVS bead 40 overlies the joint between the fabrics 31 and 32, thus completely sealing the joint.

The joint of FIG. 5 is similar to that of FIG. 4 except that a strip patch 45 is used such that the elastomer face 46 is in facing relation with elastomer faces 12B and 12 of composites 10 and 10B, the latter having fabric members 31 and 32. The stitching 35 is as described in FIG. 4, and the sealed joint is made by a patch strip 45, similar to 10B of FIG. 2, arranged over the sewn joint such that the elastomer face 46 is sealed to the opposed faces through RTVS beads 48 and 49.

The joint shown in FIG. 6 is used wherever there is stitching for various purposes such as applying decoration strips 50 to the outside surface or merely decorative stitching. In this arrangement a patch 60, similar to patch 45 is placed with the elastomer facing the elastomer of composite 61 with an RTVS bead 62,63 on each side of the stitching, which penetrates both an outer fabric 31 and the composite.

It will be apparent to those skilled in the art that various other forms of joints may be used. For example, the joints may be formed by an RTVS bead on the fabric side of the composite with the joint being made between fabric-fabric faces of facing composites or between a fabric-elastomer faces of facing composites.

Various garments may be fabricated of multiple plys of material with the composite as an intermediate ply e.g. an outer ply, an inner ply with the composite between the two plys. As a general rule the fabric elastomer composite of this invention may be sewn and handled as any other material, care being taken to seal the sewn joints as described.

Where garments need stretchability in one direction, i.e. trousers or slacks, a fabric such as the 300% by 50% material may be used, although it is preferred that the composite be 100% stretchable in each direction.

Cleaning tests of garments and other products incorporating the product of this invention have established that dry cleaning has no adverse effect on the product or any seam.

It will, accordingly, be apparent to those skilled in the art that various alterations, modifications and changes may be made to the products and techniques herein described without departing from the scope of the present invention as set forth in the appended claims.

What is claimed is:

1. A fabric elastomer composite assembly comprising:
   at least two sections of fabric elastic composite joined together by a watertight joint,
   each section of said fabric elastomer composite being composed of a stretchable fabric material joined to a vulcanizable silicone elastomeric membrane layer,
   said elastomeric membrane layer being sufficiently thin to permit passage of water vapor therethrough while preventing flow of water in liquid form therethrough, and
   said watertight joint being formed at least in part by a bond between the elastomeric component of one of said sections being bonded to an elastomeric component of another section of elastomer fabric composite.

2. An elastomeric composite assembly as set forth in claim 1 wherein said another section of elastomeric fabric composite overlies at least a portion of at least one of said sections.

3. An elastomeric composite assembly as set forth in claim 1 wherein said another section of elastomeric fabric composite is part of each of said sections and is positioned to overlie a portion of said section of which it is part.

4. An elastomeric composite assembly as set forth in claim 1 wherein said another section of elastomeric fabric composite overlies a portion of each of said sections forming said assembly.

5. An elastomeric composite assembly as set forth in claim 1 wherein said bond is formed by a vulcanizable silicone elastomer placed between the opposed elastomeric faces of the components thereby forming a bond between a joint formed by an elastomer-elastomer interface.

6. An elastomeric composite assembly as set forth in claim 1 further including at least one other fabric component associated therewith.

7. An elastomeric composite assembly as set forth in claim 1 wherein said two sections are stitched together and said watertight joint is formed by a bond at least on each side of said stitching.

8. An elastomeric composite assembly as set forth in claim 7 wherein said watertight joint is formed by a room temperature vulcanizable silicone elastomer at least on each side of said stitch.

9. A multilayered fabric material comprising:
at least a separate outer decorative fabric layer,
a fabric elastomer composite in opposed relation to said decorative fabric layer and forming at lease one inner layer of said multilayered fabric material,
said fabric elastomer composite including a relatively thin membrane layer of vulcanizable silicone elastomer material,
a stretchable fabric joined to said membrane layer;
said composite having an elongation in each direction greater than 50%,
said composite being impermeable to liquids and permeable to vapors, and
said membrane having a thickness of between 0.0006 and 0.0020 inches.

10. A multilayered fabric material as set forth in claims 9 wherein said fabric elastomer composite has a water vapor transmission rate of between 10 to 50 grams per meter squared measured at 37° C. for 24 hours.

11. A multilayered fabric material as set forth in claim 9 wherein said elastomer is a dimethylsiloxane silicone rubber.

12. A multilayered fabric material as set forth in claim 9 wherein said stretchable fabric is a nylon mesh material of not greater than 25 denier.

13. A multilayered fabric material as set forth in claim 9 wherein said composite is waterproof but water vapor permeable, flexible and stable in dry cleaning fluids.

14. A multilayered fabric material as set forth in claim 13 wherein said composite has at least 100% elongation in each direction.

* * * * *